United States Patent [19]

Ward et al.

[11] 4,185,040
[45] Jan. 22, 1980

[54] ALKYLATION OF AROMATIC HYDROCARBONS

[75] Inventors: John W. Ward, Yorba Linda; Texas V. Inwood, La Habra, both of Calif.

[73] Assignee: Union Oil Company of California, Brea, Calif.

[21] Appl. No.: 861,196

[22] Filed: Dec. 16, 1977

[51] Int. Cl.$^2$ ............................................. C07C 5/04
[52] U.S. Cl. ................................ 585/467; 252/455 Z; 252/477 R
[58] Field of Search ............ 260/671 C, 671 R; 252/455 Z, 477 R

[56] References Cited

U.S. PATENT DOCUMENTS

| | | | |
|---|---|---|---|
| 2,406,869 | 9/1946 | Upham | 260/671 C |
| 3,607,959 | 9/1971 | Estes et al. | 260/671 C |
| 3,641,177 | 2/1972 | Eberly et al. | 252/455 Z |
| 3,674,680 | 7/1972 | Hoekstra et al. | 208/112 |
| 3,769,202 | 10/1973 | Plank et al. | 252/455 Z |
| 3,776,971 | 12/1973 | Carr et al. | 260/671 R |
| 3,857,780 | 12/1974 | Gustafson | 208/139 |
| 4,028,227 | 7/1977 | Gustafson | 208/216 |
| 4,094,922 | 6/1978 | Bartek et al. | 260/671 C |

*Primary Examiner*—O. R. Vertiz
*Assistant Examiner*—Wayne A. Langel
*Attorney, Agent, or Firm*—Dean Sandford; Lannas S. Henderson; Cleveland R. Williams

[57] ABSTRACT

Highly stable and active catalysts are provided for the alkylation of aromatic hydrocarbons with $C_2$-$C_4$ olefins. The catalysts are extruded composites of an acidic, crystalline aluminosilicate zeolite, e.g. Y zeolite, and a porous mineral oxide binder. The basic novel feature of the invention resides in the shape and size of the catalyst extrudates. By shaping the extrudates so as to give a high ratio of external surface area to volume, resistance to deactivation is found to be much improved, as well as activity and selectivity.

16 Claims, No Drawings

ALKYLATION OF AROMATIC HYDROCARBONS

BACKGROUND AND SUMMARY OF INVENTION

Processes utilizing corrosive Friedel-Crafts type catalysts for the alkylation of aromatic hydrocarbons have long been known, and are still widely practiced commercially. It has been known for some time that the principal disadvantages of such processes can be avoided by the use of acidic, crystalline aluminosilicate zeolite catalysts, which are non-corrosive and from which the alkylation products can be more readily separated.

In using solid zeolite catalysts, two principal modes of operation have been described. Firstly, the catalyst may be utilized as a powder slurried in the liquid reactants. This procedure is disadvantageous because it generally requires batch as opposed to continuous operation, and also requires expensive filtration or centrifuging units to separate catalyst from products. A much more commercially feasible technique involves the use of a fixed bed of relatively large catalyst particles through which the reactants are continuously passed. A first practical requirement in such fixed bed operations is that the catalyst particles must be sufficiently large to permit passage of reactants through the bed without developing a prohibitive pressure drop therethrough. This requirement can in turn place limitations on the efficiency of utilization of active sites located in the interior of the catalyst particles, which are accessible only by diffusion through macropores in the outer layers of the catalyst particles.

In certain fixed-bed processes utilizing catalysts containing an active hydrogenating metal and carried out in the presence of high pressure hydrogen, it has been disclosed that pressure drop can be minimized while obtaining increased bulk-volume catalyst activity by forming the catalyst particles into various non-cylindrical shapes which exhibit an increased ratio of exterior surface area to volume, and which form packed beds having increased void space. These processes include catalytic hydrofining of mineral oils to remove sulfur and nitrogen compounds (U.S. Pat. Nos. 3,674,680, 3,990,964 and 4,028,227) and catalytic hydroforming of naphthas (U.S. Pat. No. 3,857,780). Typical catalyst particles described are extrudates whose cross sections embrace a plurality of arcuate lobes extending outwardly from the central portion thereof in cloverleaf fashion.

Although an increase in the exterior surface area/volume ratio of porous catalyst particles (as by decreasing size or modifying shape) might be expected to give some increase in fresh activity, it does not follow that such increased activity would be of a significant magnitude in all cases, or that a concomitant increase in deactivation rate might not completely outweigh any improvement in fresh activity. In most hydrocarbon conversion processes, including alkylation, the principal catalyst-deactivating factor resides in the deposition of polymers, or coke-like materials on the active catalyst surfaces. In cases such as those discussed above, wherein hydrogen and a catalytic metal are present, the formation of polymers and coke can be suppressed almost to an equilibrium value by hydrogenation of coke and polymer precursors. However, in alkylation with olefins as herein, hydrogen is necessarily absent, and the catalyst contains no hydrogenating metal. In our initial investigation of alkylation with zeolite catalysts, we found that catalyst deactivation rates were a much more serious problem than was initial activity. The zeolite catalysts contain no known polymerization-suppressing component; their acid function promotes both alkylation and polymer formation. It was hence uncertain as to whether initial activity could be improved without aggravating the more serious problem of catalyst deactivation rates.

This deactivation problem is well-recognized in the art, and it has been fairly well established that the mechanism thereof involves polymerization of the olefin, followed by hydrogen-transfer and cyclization reactions to form large aromatic molecules which cannot diffuse out of the crystal micropores of the zeolite in which the active sites are located. (Venuto et al, *J. Catalysis* 5, 484–493, 1966; *I and EC Product Research and Development*, 6, 190–192, Sept. 1967). The rate of such deactivation is in direct proportion to the concentration of olefin in the interior of the catalyst particles. In order to minimize olefin polymerization and polyalkylation of the aromatic hydrocarbon, it is customary in such alkylations to utilize a feed mixture comprising about 4–10 moles of aromatic hydrocarbon per mole of olefin. When using catalyst particles of the usual commercial size and shape, e.g. 1/16" cylindrical extrudates, the diffusion of such feed mixtures into each catalyst particle via its interstitial macropore structure, and the resultant depletion of olefin by alkylation, establishes a concentration gradient of olefin in each particle—high near the exterior surface thereof and low in the interior. This would be expected to establish a zone of rapid deactivation in the outer shell of the particle, which zone would gradually shift toward the interior, assuming no substantial blockage of the interstitial macropores.

In view of all the foregoing, it would appear that any reduction in particle size, or change in shape to give a lower ratio of volume to exterior surface area, would result in an increase in average olefin concentration therein (by reducing the olefin concentration gradient). This in turn would be expected to act in the direction of increasing the deactivation rate of each particle, and this would not be expected to increase the cycle life of a bed of catalyst particles. We have discovered however that a substantial such increase is obtained; apparently some other operative factor is brought into play when the volume/surface area ratio is decreased which actually leads to a substantial decrease in deactivation rate and an increase in cycle life. At the same time there is a significant increase in bulk volume activity and selectivity of conversion to monoalkylated products.

PRIOR ART

1. U.S. Pat. No. 3,641,177 discloses the use of steam stabilized hydrogen Y and rare earth-hydrogen Y zeolites containing less than 1% Na for catalyzing the alkylation of benzene with olefins. The catalyst is utilized as a powder slurried in the liquid reactants. There is no disclosure of catalyst particle sizes or shapes for fixed-bed operations.

2. U.S. Pat. No. 3,776,971 discloses the use of hydrogen Y and rare earth Y zeolites containing about 1.8 wt.% $Na_2O$ (column 3, lines 10–20) for catalyzing the alkylation of benzene with propylene or ethylene. The catalyst is utilized as a fixed bed of mixed 10–20 mesh size range granules. There is no teaching of using catalyst particles of uniform size—necessary to minimize pressure drop.

3. U.S. Pat. No. 3,674,680 discloses hydrodesulfurization of resid oils using alumina-based Co-Mo catalysts shaped in various forms to provide a surface/volume ratio of 100-250 in$^{-1}$. There is no teaching of zeolite catalysts or of decreasing catalyst deactivation rates as a result of catalyst shaping.

4. U.S. Pat. No. 3,857,780 discloses hydroforming of naphthas using metal-promoted alumina extrudate catalyst particles having polylobal cross sections. There is no suggestion of decreased deactivation rates.

5. U.S. Pat. No. 4,028,227 discloses hydrodesulfurization of resid oils using Co—Mo—Al$_2$O$_3$ catalyst extrudates shaped to provide increased activity, substantially as disclosed in the preceding two patents. An improvement in deactivation rates is attributed only to a modification of prior art catalyst pore sizes (Example 2).

DETAILED DESCRIPTION

The active zeolites employed herein are now well known in the art, consisting of crystalline aluminosilicates having SiO$_2$/Al$_2$O$_3$ mole ratios between about 2 and 80, preferably about 4-12, and a predominance of crystal pore volume in pores having diameters between about 5 and 15 Å. A critical aspect of the invention resides in substantially completely removing zeolitic alkali metal and alkaline earth metals from the zeolite, and replacing such metals with hydrogen ions and/or rare earth metals. The Na$_2$O content of the zeolite should be less than about 0.7%, preferably less than about 0.5% by weight. Only highly acidic zeolites of this nature possess the desired activity—and the concomitant high deactivation rates which the present invention is designed to control.

Examples of suitable zeolites include molecular sieves of the X, Y, L, B,·ZSM-5 and Omega crystal types, as well as mordenite, chabazite and the like. A much preferred zeolite is steam stabilized hydrogen Y zeolite having a unit cell size between about 24.40 and 24.64 Å, and having been prepared by the method described in U.S. Pat. No. 3,929,672, the disclosure of which is incorporated herein by reference.

In order to prepare mechanically stable extrudates of the crystalline zeolites, a porous mineral oxide binder is utilized, such as alumina gel, silica-gel, silica-alumina cogels, plastic acid-washed clays, titania, zirconia and the like, with alumina being preferred. Ordinarily the finished catalyst comprises about 3-50%, preferably about 5-30% by weight of the binder, which serves not only to strengthen the extrudates, but to provide a porous matrix comprising macropores in the 300-1000 Å diameter range. These macropores can be regarded as "freeways", giving improved diffusional access to the interior of the extrudates.

To meet the basic requirement for extrudates having a ratio of exterior surface area to volume within the 85-160 in$^{-1}$ range, or the preferred 90-150 in$^{-1}$ range, either of two alternatives may be adopted.

The non-preferred alternative consists in using cylindrical extrudates of less than 1/16" diameter. A 1/32" diameter cylindrical extrudate for example has a surface/volume ratio of about 140 in$^{-1}$. However, the use of such small diameter cylindrical extrudates can lead to pressure drop problems and excessive breakage, especially when utilizing deep beds of catalyst. Both of these problems can however be alleviated by using catalyst beds having low length/diameter (L/D) ratios. Shallow catalyst beds obviously will reduce breakage, and at any given space velocity there will be a lower mass velocity of fluid reactants, which in turn reduces pressure drop. (Mass velocity is defined as pounds of total feed per square foot of reactor cross section per hour.)

However, it is usually desirable to maintain fairly high mass velocities, and, for uniform feed distribution and reactor design reasons, fairly deep catalyst beds. For these reasons it is preferred to utilize non-cylindrical extrudates having a cross sectional configuration embracing a plurality of arcuate lobes extending outwardly from the central portion thereof, as illustrated for example in FIGS. 6, 7, 8, and 10 of U.S. Pat. No. 4,028,227. These configurations lend strength to the extrudates and also provide more interstitial void space in the catalyst bed, thereby reducing pressure drop.

To summarize, it is found that the following combinations of catalyst dimensions are optimum from the standpoint of the best compromise between catalyst activity, deactivation rates, pressure drop and catalyst breakage:

| | Catalyst Dimensions, Inches | |
|---|---|---|
| | Broad Range | Preferred Range |
| Length | 0.1-0.25 | 0.12-0.2 |
| Diameter (Max.) | 0.03-0.08 | 0.04-0.07 |
| Ratio, External Surface Area/Vol., in$^{-1}$ | 85-160 | 90-150 |

In the case of cylindrical extrudates, there will of course be only one cross-sectional diameter. In the case of non-cylindrical extrudates, the maximum diameter in the above table is the maximum possible length of a chord traversing the cross section and wholly included within the boundaries thereof, whether or not such chord passes through the center of the cross section.

An especially preferred catalyst shape for use herein is one having a "trilobal" or three-leaf clover type of cross section, such as that illustrated for example in FIG. 8 of U.S. Pat. No. 4,028,227. For purposes of the present invention such a cross-sectional shape may be defined as a symmetrical trilobe in which the perimeter of each lobe is defined by a 180°-270° arc of a circle having a diameter between about 0.02 and 0.04 inches. The 180° arc trilobe is optimum from the standpoint of mechanical strength, but packed beds thereof are deficient in void space, thus presenting pressure drop problems. The 270° arc trilobe is optimum from the pressure drop standpoint, but is somewhat fragile in that the lobes tend to break away from each other. An optimum combination of properties appears to be exhibited by trilobe extrudates wherein each lobe is defined by a 210°-250° arc.

Another important aspect of the invention resides in tailoring the catalyst bed with catalyst particles of substantially uniform size. Any substantial non-uniformity in catalyst particle size results in decreased void space, with resultant increased pressure drop, as compared to the void space and resultant pressure drop which would prevail if the particles were uniform in size, irrespective of the absolute dimensions of the particles. Accordingly, the extrudates should have essentially the same maximum diameter, and at least about 90% of the extrudates should vary in length no more than about ±25% from their average length.

The alkylation process itself is carried out in conventional fashion, with the reactants being passed upwardly, or preferably downwardly, through the catalyst bed. A mole excess of aromatic hydrocarbon is utilized in order to minimize the formation of olefin polymers and polyalkylated products. The olefin is essentially completely consumed, and the reactor effluent is fractionated to recover unreacted aromatic hydrocarbon for recycle, the desired alkylated product, and a minor proportion of polyalkylated product which may be recycled to suppress any net production of undesired polyalkylated compounds. The process conditions may fall within the following ranges:

| | Alkylation Conditions | |
|---|---|---|
| | Broad Range | Preferred Range |
| Temp., °F. | 200–900 | 300–600 |
| Pressure, psig | 150–2000 | 400–1500 |
| Total WHSV | 2–2000 | 4–100 |
| Aromatic/olefin mole/ratio | 2–20 | 4–15 |
| Mass velocity | 50–3000 | 200–2000 |

The conditions of temperature and pressure should be correlated so that at least some liquid phase is present, at least until substantially all the olefin is consumed. Rapid catalyst deactivation occurs under most alkylating conditions when no liquid phase is present, presumably due to the deposition on the catalyst of polymer precursors which are not washed away.

Aromatic hydrocarbons which may be alkylated herein include benzene, toluene, xylenes, cumene, ethylbenzene, naphthalene, etc. The $C_2$-$C_4$ olefins employed comprise ethylene, propylene, isobutene and n-butene, or mixtures thereof. Usually a monoalkylated product is desired, but polyalkylated products can also be produced by appropriate recycle of the unwanted alkylates. The process is especially useful for the production of ethylbenzene from benzene and ethylene, and cumene from benzene and propylene.

The following examples are illustrative of the invention:

EXAMPLE 1

Two catalysts, A and B, having the same composition were prepared by comulling about 10 weight-percent (dry basis) of an alumina hydrogel with 90 weight-percent of a steam stabilized ammonium Y zeolite containing about 0.2% $Na_2O$ and having been prepared by the method described in U.S. Pat. No. 3,929,672. The comulled mixture was then formed into extrudates in conventional manner, catalyst A by extrusion through a circular 1/16" diameter die, and catalyst B by extrusion through a die having a three-leaf clover shaped orifice having a maximum diameter of 1/16". After drying and calcining at 860° F., the cylindrical extrudate particles A were found to have an average surface/volume ratio of 81.7 in$^{-1}$, while the trilobe extrudate particles B had an average ratio of 109 in$^{-1}$.

EXAMPLE 2

Eighty ml of catalyst A (mixed with about 160 ml of quartz chips) was loaded into a 1-inch I.D. reactor. A bed of quartz chips was provided above the catalyst bed for preheating the feed. The entire reactor was enclosed within a heated sand bath. Temperature profile in the catalyst bed was monitored by a vertically movable thermocouple. A 20-day alkylation run was then carried out in which benzene was continuously ethylated with a mixture of 16 mol.% ethylene in methane (simulating an FCC off-gas). The conditions of the run were as follows:

| | |
|---|---|
| Sand Bath Temperature | 440° F. |
| Pressure | 950 psig |
| Total WHSV | 7.5 |
| Benzene/Ethylene mole ratio | 10/1 |

Under these conditions the ethylene was substantially completely consumed in the upper portion of the catalyst bed, as evidenced by a peak in the temperature profile. This peak exceeds the sand bath temperature by about 30°–40° F., and results from the exothermic alkylation of benzene with ethylene. After substantial depletion of ethylene, the peak temperature drops off essentially to the sand bath temperature. After 5 days of operation, the peak temperature was located at a level 23% down in the catalyst bed. During the next 15 days of operation the peak moved downwardly at an essentially linear average rate to a level 33% down in the catalyst bed. This downward shift in the position of the peak temperature provides a measure of the catalyst deactivation rate. In the present example the 5–15 day shift shows that an average of about 0.666% per day of the catalyst bed was being deactivated. This indicates a cycle life of about 119 days before breakthrough of ethylene in the reactor effluent.

At the end of the 20 day run, the selectivity of conversion of ethylene to ethylbenzene was 89.6%, and of ethylene to ethylbenzene-plus-diethylbenzene, 97.6%.

EXAMPLE 3

Another 20-day alkylation run was carried out in the same manner as described in Example 2, catalyst A being replaced with the same volume of the trilobe catalyst B. After 5 days of this run the peak temperature was located 13% down the catalyst bed, and during the next 15 days shifted downwardly at an essentially linear average rate to a level of 16.5% down the catalyst bed. This downward shift shows that an average of about 0.233% per day of the catalyst bed was being deactivated. This indicates a cycle life of about 390 days, over three times the projected cycle life for catalyst A.

In addition to improved life, improved 20-day selectivities were observed: 91.6% conversion of ethylene to ethylbenzene, and 98.3% conversion to ethylbenzene-plus-diethylbenzene.

The following claims and their obvious equivalents are believed to define the true scope of the invention.

We claim:

1. An alkylation process which comprises passing a mixture of a $C_2$-$C_4$ olefin and a mole-excess of an alkylatable aromatic hydrocarbon through a fixed bed of an alkylation catalyst under alkylating conditions and recovering a desired alkylated hydrocarbon from the resulting product, said alkylation catalyst consisting essentially of a composite of an acidic crystalline aluminosilicate zeolite containing less than about 0.7 wt.% of $Na_2O$ and a porous mineral oxide binder, said composite being in the form of substantially uniform sized extrudates having a maximum overall diameter between 0.03 and 0.08 inch, a length between 0.1 and 0.25 inch, and having a ratio of external surface area to volume of between 85 and 160 reciprocal inches.

2. A process as defined in claim 1 wherein said aluminosilicate zeolite is a steam stabilized hydrogen Y zeolite having a unit cell size between about 24.40 and 24.64 Å, and said mineral oxide binder is alumina.

3. A process as defined in claim 2 wherein the cross section of said extrudates embraces a plurality of arcuate lobes extending outwardly from the central portion thereof.

4. A process as defined in claim 2 wherein the cross section of said extrudates is in the shape of a trilobe wherein each lobe is defined by a 180°–270° arc of a circle having a diameter between about 0.02 and 0.04 inches.

5. A process as defined in claim 1 wherein the alkylating conditions of temperature and pressure are controlled to provide a liquid phase in the contacting zone.

6. A process as defined in claim 1 wherein the ratio of external surface area to volume of said extrudates is between about 90 and 150 reciprocal inches.

7. A process as defined in claim 1 wherein the cross section of said extrudates embraces a plurality of arcuate lobes extending outwardly from the central portion thereof.

8. A process as defined in claim 1 wherein the cross section of said extrudates is in the shape of a trilobe wherein each lobe is defined by a 180°–270° arc of a circle having a diameter between about 0.02 and 0.04 inches.

9. A process for the manufacture of ethylbenzene which comprises passing a mixture of ethylene and a mole-excess of benzene through a fixed bed of an alkylation catalyst under alkylating conditions and recovering ethylbenzene from the resulting product, said alkylation catalyst consisting essentially of a composite of an acidic crystalline aluminosilicate zeolite containing less than about 0.7 wt.% of $Na_2O$ and a porous mineral oxide binder, said composite being in the form of substantially uniform sized extrudates having a maximum overall diameter between 0.03 and 0.08 inch, a length between 0.1 and 0.25 inch, and having a ratio of external surface area to volume of between 85 and 160 reciprocal inches.

10. A process as defined in claim 9 wherein said aluminosilicate zeolite is a steam stabilized hydrogen Y zeolite having a unit cell size between about 24.40 and 24.64 Å, and said mineral oxide binder is alumina.

11. A process as defined in claim 10 wherein the cross section of said extrudates embraces a plurality of arcuate lobes extending outwardly from the central portion thereof.

12. A process as defined in claim 10 wherein the cross section of said extrudates is in the shape of a trilobe wherein each lobe is defined by a 180°–270° arc of a circle having a diameter between about 0.02 and 0.04 inches.

13. A process as defined in claim 9 wherein the alkylating conditions of temperature and pressure are controlled to provide a liquid phase in the contacting zone.

14. A process as defined in claim 9 wherein the ratio of external surface area to volume of said extrudates is between about 90 and 150 reciprocal inches.

15. A process as defined in claim 9 wherein the cross section of said extrudates embraces a plurality of arcuate lobes extending outwardly from the central portion thereof.

16. A process as defined in claim 9 wherein the cross section of said extrudates is in the shape of a trilobe wherein each lobe is defined by a 180°–270° arc of a circle having a diameter between about 0.02 and 0.04 inches.

* * * * *